US008940026B2

(12) United States Patent
Hilse et al.

(10) Patent No.: US 8,940,026 B2
(45) Date of Patent: Jan. 27, 2015

(54) APPARATUS FOR THE CONSTANT-ANGLE FIXATION AND COMPRESSION OF A FRACTURE OR OSTEOTOMY OF A BONE

(75) Inventors: Martin Hilse, Berlin (DE); Curt Kranz, Berlin (DE); Susanne Kahl, legal representative, Berlin (DE); Emmanuel Anapliotis, Berlin (DE)

(73) Assignee: Merete Medical GmbH, Berlin (DE)

( * ) Notice: Subject to any disclaimer, the term of this patent is extended or adjusted under 35 U.S.C. 154(b) by 214 days.

(21) Appl. No.: 13/263,037

(22) PCT Filed: Mar. 30, 2010

(86) PCT No.: PCT/DE2010/000365
§ 371 (c)(1),
(2), (4) Date: Jun. 5, 2012

(87) PCT Pub. No.: WO2010/115403
PCT Pub. Date: Oct. 14, 2010

(65) Prior Publication Data
US 2012/0265255 A1    Oct. 18, 2012

(30) Foreign Application Priority Data
Apr. 7, 2009  (DE) .......................... 10 2009 016 394

(51) Int. Cl.
*A61B 17/80*     (2006.01)
(52) U.S. Cl.
CPC ......... *A61B 17/8014* (2013.01); *A61B 17/8057* (2013.01)
USPC .......................................... 606/282; 606/291
(58) Field of Classification Search
USPC .................................................. 606/280–299
See application file for complete search history.

(56) References Cited

U.S. PATENT DOCUMENTS

| 2,662,988 A | 12/1935 | McKim |
| 3,741,205 A | 6/1973 | Markolf et al. |

(Continued)

FOREIGN PATENT DOCUMENTS

| AT | 406446 | 5/2000 |
| DE | 31 13 639 | 5/1982 |

(Continued)

OTHER PUBLICATIONS

Easley, Mark E., M.D., et al., Current Concepts Review: Hallux Valgus Part II: Operative Treatment, Foot & Ankle International, vol. 28/ No. 6, 748-758 (Jun. 2007).

(Continued)

*Primary Examiner* — Michael T Schaper
*Assistant Examiner* — Tracy Kamikawa
(74) *Attorney, Agent, or Firm* — Andrus Intellectual Property Law, LLP

(57) ABSTRACT

Apparatus for the fixed-angle fixation and compression of a fracture site or osteotomy of a bone includes a bone plate having a plurality of holes and bone screws with a threaded head. The bone screws accommodated in the holes are screwed into the bone. At least one of the holes is a combination of two circular holes of different diameter. As screwing of the bone screw into the bone proceeds through a final stage, engagement of the threads on the head with threads in the combination hole effects relative longitudinal displacement between the plate and the bone whereby it is possible to simplify simultaneous fixed angle fixation and compression of the fracture or osteotomy with use of a single screw. Threads on the head of the bone screw engage threads in the hole which is a combination of the two hole to effect relative motions.

9 Claims, 6 Drawing Sheets

(56) References Cited

U.S. PATENT DOCUMENTS

| | | |
|---|---|---|
| 3,757,591 A | 9/1973 | Taylor |
| 4,408,601 A | 10/1983 | Wenk |
| 4,454,876 A | 6/1984 | Mears |
| 4,616,634 A | 10/1986 | Vargas Garcia |
| 4,720,225 A | 1/1988 | Burt |
| 4,903,691 A | 2/1990 | Heinl |
| 4,959,065 A | 9/1990 | Arnett et al. |
| 5,529,075 A | 6/1996 | Clark |
| 5,709,686 A | 1/1998 | Talos et al. |
| 6,129,728 A | 10/2000 | Schumacher et al. |
| 6,203,545 B1 | 3/2001 | Stoffella |
| 6,206,883 B1 | 3/2001 | Tunc |
| 6,306,140 B1 | 10/2001 | Siddiqui |
| 6,398,783 B1* | 6/2002 | Michelson ............. 606/70 |
| 6,423,068 B1 | 7/2002 | Reisberg et al. |
| 6,669,701 B2 | 12/2003 | Steiner et al. |
| 6,716,957 B2 | 4/2004 | Tunc |
| 6,719,759 B2 | 4/2004 | Wagner et al. |
| 6,730,091 B1 | 5/2004 | Pfefferle et al. |
| 6,886,799 B2 | 5/2005 | Yamanashi |
| 7,008,428 B2 | 3/2006 | Cachia et al. |
| 7,354,441 B2 | 4/2008 | Frigg |
| 7,468,069 B2 | 12/2008 | Baynham et al. |
| 7,655,029 B2 | 2/2010 | Niederberger et al. |
| 7,771,457 B2 | 8/2010 | Kay et al. |
| 7,976,570 B2 | 7/2011 | Wagner et al. |
| 8,118,848 B2 | 2/2012 | Ducharme et al. |
| 8,246,661 B2 | 8/2012 | Beutter et al. |
| 8,632,545 B2 | 1/2014 | Sarangapani et al. |
| 2002/0045897 A1 | 4/2002 | Dixon et al. |
| 2002/0045901 A1 | 4/2002 | Wagner et al. |
| 2002/0183752 A1 | 12/2002 | Steiner et al. |
| 2003/0078668 A1 | 4/2003 | Michelson |
| 2004/0018228 A1 | 1/2004 | Fischell et al. |
| 2004/0034356 A1 | 2/2004 | LeHuec et al. |
| 2004/0073218 A1 | 4/2004 | Dahners |
| 2004/0102778 A1 | 5/2004 | Huebner et al. |
| 2004/0167522 A1* | 8/2004 | Niederberger et al. ......... 606/69 |
| 2004/0215192 A1 | 10/2004 | Justis et al. |
| 2004/0236332 A1 | 11/2004 | Frigg |
| 2005/0015092 A1 | 1/2005 | Rathbun et al. |
| 2005/0049594 A1* | 3/2005 | Wack et al. ............. 606/69 |
| 2005/0065521 A1 | 3/2005 | Steger et al. |
| 2005/0085818 A1 | 4/2005 | Huebner |
| 2005/0124994 A1 | 6/2005 | Berger et al. |
| 2005/0165400 A1 | 7/2005 | Fernandez |
| 2005/0165401 A1 | 7/2005 | Pack |
| 2005/0182408 A1* | 8/2005 | Pfefferle et al. ............. 606/69 |
| 2005/0192577 A1 | 9/2005 | Mosca et al. |
| 2005/0261688 A1 | 11/2005 | Grady, Jr. et al. |
| 2006/0235396 A1 | 10/2006 | Sanders et al. |
| 2006/0241607 A1 | 10/2006 | Myerson et al. |
| 2007/0016205 A1 | 1/2007 | Beutter et al. |
| 2007/0123885 A1 | 5/2007 | Kirschman |
| 2007/0233106 A1 | 10/2007 | Horan et al. |
| 2007/0276386 A1 | 11/2007 | Gerlach et al. |
| 2008/0051786 A1 | 2/2008 | Jensen |
| 2008/0132955 A1 | 6/2008 | Frigg |
| 2009/0024172 A1 | 1/2009 | Pizzicara |
| 2009/0210010 A1 | 8/2009 | Strnad et al. |
| 2011/0295325 A1 | 12/2011 | Wagner et al. |
| 2012/0265254 A1 | 10/2012 | Horan et al. |
| 2013/0190829 A1 | 7/2013 | Batsch et al. |

FOREIGN PATENT DOCUMENTS

| | | |
|---|---|---|
| DE | 102005044841 | 3/2006 |
| DE | 102006000948 | 10/2006 |
| DE | 102005042766 | 1/2007 |
| DE | 102005043285 | 1/2007 |
| DE | 69835968 | 5/2007 |
| DE | 102010025001 | 12/2011 |
| EP | 0243114 | 11/1990 |
| EP | 1 255 498 | 11/2002 |
| EP | 1158916 | 7/2004 |
| EP | 1158915 | 9/2004 |
| EP | 1 468 655 | 10/2004 |
| EP | 1255498 | 11/2005 |
| EP | 1677693 | 7/2006 |
| EP | 1468655 | 5/2008 |
| EP | 1702577 | 11/2008 |
| EP | 2 016 918 | 1/2009 |
| FR | 2667913 | 4/1992 |
| FR | 2739151 | 3/1997 |
| FR | 2886535 | 12/2006 |
| WO | 9709000 | 3/1997 |
| WO | 0053110 | 9/2000 |
| WO | 0154601 | 8/2001 |
| WO | WO-02/096309 | 12/2002 |
| WO | 2005041796 | 5/2005 |
| WO | 2005053111 | 6/2005 |
| WO | 2006014436 | 2/2006 |
| WO | 2007025520 | 3/2007 |
| WO | 2012/000627 | 5/2012 |

OTHER PUBLICATIONS

Iselin, Lukas D. et al., Operative Management of Common Forefoot Deformities a Representative Survey of Australian Orthopaedic Surgeons, Foot & Ankle Specialist, vol. X/ No. X, 1-7 (2012).

Miller, Michael J., DMP et al., Inverted Z-scarf Osteotomy for Hallux Valgus Deformity Correction: Intermediate-term Results in 55 Patients, The Journal of Foot and Ankle Surgery, 50: 55-61 (2011).

Dereymaeker, Greta, MD, PhD, Scarf Osteotomy for Correction of Hallux Valgus—Surgical Technique and Results as Compared to Distal Cheveron Osteotomy, The Hallux, vol. 5/ No. 3, 513-523 (Sep. 2000).

Steck, Jerome K., DPM, Long Z-Osteotomy: A Review and New Modification to Correct Troughing, The Journal of Foot and Ankle Surgery, vol. 40/ No. 5, 305-310 (Sep./Oct. 2001).

Adam, Stephanie P., DO et al., Outcomes after Scarf Osteotomy for Treatment of Adult Hallux Valgus Deformity, Clinical Orthopaedics and Related Research, 469: 854-859 (2011).

Trnka, Hans-Jorg, MD et al., Six First Metatarsal Shaft Osteotomies—Mechanical and Immobilization Comparisons, Clinical Orthopaedics and Related Research, No. 381, 256-265 (Mar. 10, 2000).

Aminian, Arash, M.D. et al., Scarf Osteotomy for Hallux Valgus Deformity: An Intermediate Followup of Clinical and Radiographic Outcomes, Foot & Ankle International, vol. 27/ No. 11, 883-886 (Nov. 2006).

Weil, Lowell Scott, DPM, Scarf Osteotomy for Correction of Hallux Valgus—Historical Perspective, Surgical Technique, and Results, The Hallux, vol. 5/ No. 3, 559-580 (Sep. 2000).

Vienne, Patrick, M.D. et al, Comparative Mechanical Testing of Different Geometric Designs of Distal First Metatarsal Osteotomies, Foot & Ankle International, vol. 28/ No. 2, 232-236 (Feb. 2007).

Lipscombe, Stephen, MRCS et al, Scarf Osteotomy for the Correction of Hallux Valugs: Midterm Clinical Outcome, The Journal of Food and Ankle Surgery, vol. 47/ No. 4, 273-277 ( Jul./Aug. 2008).

Barouk, Louis Samuel, MD, Scarf Osteotomy for Hallux Valgus Correction—Local Anatomy, Surgical Technique, and Combination with Other Forefoot Procedures, The Hallux, vol. 5/ No. 3, 525-557 (Sep. 2000).

Crevoisier, Xavier et al., The Scarf Osteotomy for the Treatment of Hallux Valgus Deformity: A Review of 84 Cases, Foot & Ankle International, vol. 221 No. 12, 970-976 (Dec. 2001).

Coetzee, J. Chris, M.D., Scarf Osteotomy for Hallux Valgus Repair: The Dark Side, Foot & Ankle International, vol. 24/ No. 1, 29-33 (Jan. 2003).

Interventional Procedures Programme—Interventional procedure overview of surgical correction of hallux valgus using minimal access techniques, National Institute for Health and Clinical Excellence, p. 1, 9.

Comparison of Preoperative to Postoperative Measurement at 6 Weeks, 1 and 2 Years Postoperative, Table 1.

O'Briain, David E. et al., Use of a Geometric Formula to Improve the Radiographic Correction Achieved by the Scarf Osteotomy, Foot & Ankle International, vol. 33/ No. 8, 647-654 (Aug. 2012).

(56) References Cited

OTHER PUBLICATIONS

International Search Report for PCT/DE2010/075167, mailed Apr. 15, 2011.

Acevedo, Jorge I, Sammarco, V. James, Boucher, Henry R., Parks, Bert G., Schon, Lew C., Myerson, Mark S; Mechanical Comparison of Cyclic Loading in Five Different First Metatarsal Shaft Osteotomies; Foot & Ankle International, Aug. 2002; vol. 23, No. 8, pp. 711-716.

Cisar, J., Holz, U, Jenninger, w., Uhlig. Chr.; Die Osteotomie nach Ludloff bei der Hallux-valgus-Operation; Aktuelle Traumatol. 13; 1983; pp. 247-249.

Hyer, Christopher F., Glover, Jason P., Berlet, Gregory C., Philbin, Terrence, M, Lee, Thomas H.; A Comparison of the Crescentic and Mau Osteotomies for Correction of Hallux Valgus; Journal of Foot and Ankle Surgery; Mar./Apr. 2008; vol. 47, No. 2,; pp. 103-111.

Ludloff, Prof. Dr. K.; Die Beseitigung des Hallux valgus durch die schrage planta-dorsale Osteotomie des Metatarus I.; Arch. Klin. Chir.; 110:364-387; 1918.

Mau, C., Lauber, H.J.; Die operative Behandlung des Hallux valgus (Nachuntersuchungen); 1926, 197:361-377.

Sammarco, V. James; Surgical Strategies: Mau Osteotomy for Correction of Moderate and Severe Hallux Valgus Deformity; Foot & Ankle International; Jul. 2007; 28(7); pp. 857-864.

Saxena, Amol, McCammon, Derek; The Ludloff Osteotomy: A Critical Analysis; Journal of Foot and Ankle Surgery; 1997; vol. 36, No. 2, pp. 100-105.

Trnka, H.-J., Hofstaetter, S.G., Hofstaetter, J.G., Gruber, F., Adams Jr., S.B., Easley, M.E.; Intermediate-Term Results of the Ludloff Osteotomy in One Hundred and Eleven Feet; The Journal of Bone and Joint Surgery; Mar. 2008; vol. 90-A(3); pp. 531-539.

International Search Report for PCT/2006/001508, mailed Feb. 8, 2007.

"Orthopaedic Product News", Aug. 2005, Retrieved from the Internet: URL:http://www.orthoworld.com/us_opn-2005-08.pdf [retrieved on May 26, 2009], p. 30, Hallux Valgus Correction with a Low Profile Locking Plate.

\* cited by examiner

APPARATUS FOR THE CONSTANT-ANGLE FIXATION AND COMPRESSION OF A FRACTURE OR OSTEOTOMY OF A BONE

BACKGROUND OF THE INVENTION

The invention relates to an apparatus for the fixed-angle fixation and compression of a fracture site or osteotomy of a bone.

EP 1 255 498 B1 makes known a bone plate which can be used either for compression or fixation to treat bone fractures. This is achieved by this known prior art in that the bone plate has a top side, an underside intended for contact with the bone, and a plurality of holes for receiving bone screws, these holes being located along the longitudinal axis of the plate and connecting the top side and the underside, wherein at least one of the holes is composed of a combination of a circular hole having an elongated hole. The distance between the centers of symmetry of the circular hole and the elongated hole is shorter than the sum of the radius of the circular hole and half of the longitudinal axis of the elongated hole. An elongated hole as defined by this known prior art is an oval, ellipsoidal, or rectangular hole, or a combination of such shapes as an elongated hole, but circular holes are excluded.

This known prior art can generate either only compression or fixation. Compression is attained by way of longitudinal displacement of the fracture elements when the bone screw is tightened in the elongated hole. It does not simultaneously bring about fixed-angle fixation, however. This can be attained only by using a separate bone screw in another elongated hole, and so a large number of bone screws must be used. Treatment of the fracture is complex and complicates the patient's surgery.

Furthermore, DE 31 13 639 A1 makes known an osteosynthetic compression plate comprising a plurality of slot-type holes located in the longitudinal direction of the plate, the holes comprising contact surfaces for countersunk bone screws having a spherical head. The compression of the fracture is achieved here by way of a displacement motion of the two bone parts, wherein the spherical head of the countersunk bone screw glides in the longitudinal direction of the plate along a conical or spherical countersink within the slot-type holes. A further bone screw is used for fixation in the position that has been compressed in this manner. This prior art therefore does not differ from that mentioned previously.

WO 02/096309 A1 describes a bone plate for fixing fractures of the proximal humerus, comprising a stem-shaped part, the length of which is greater than the width thereof, and a spoon-shaped part, the width of which is greater than the width of the stem-shaped part, wherein the stem-shaped part and the spoon-shaped part have a common longitudinal central axis. The holes in the stem-shaped part comprise a combination of a hole having a larger diameter and a hole having a smaller diameter, wherein at least one of the screw holes has an at least partial internal thread.

Simultaneous compression and fixation within a screw hole is likewise not possible with this known prior art.

SUMMARY OF THE INVENTION

In view of this prior art, the object of the invention is to provide a device for the fixed-angle fixation and compression of a fracture site or osteotomy of a bone, which makes it possible to simplify the fixed-angle fixation and compression of the fracture site and achieve both functions at the same time using a single bone screw.

According to the invention, the fixation function and the compression function within a screw hole can be performed by a single bone screw. For the patient, this provides the extraordinary advantage that the number of bone screws used to treat the fracture can be greatly reduced, the bone is perforated less, dimensions of the bone plates can be reduced, and the surgery can be simplified.

The apparatus according to the invention comprises a bone plate having a top side, an underside and a plurality of holes which connect the top side and the underside and are located in the longitudinal axis of the plate, and bone screws having a threaded head which are accommodated in the holes and screwed into the bone, wherein at least one hole is a combination of two circular holes having radii that differ in size, and the centers of symmetry of the two holes are located on the longitudinal axis of the bone plate. The fixation and compression functions are combined in that the circular holes are located with offset relative to one another in the direction of the longitudinal axis such that a circular section of the small hole forms a one-sided, crescent-shaped expansion, which is shouldered by edges, on the circumference of the large hole, wherein the center of symmetry of the small hole is located close to the center of symmetry of the large hole, and the distance A between the two centers of symmetry fulfills the condition $\frac{1}{18} D2 < A < \frac{1}{3} D2$, D2 being the small diameter, and the inner wall of the large hole is provided with an internal thread that runs from the top side to the underside and extends to the edges, and the crescent-shaped expansion is designed without a thread, wherein the bone screw fixes the bone in the center of symmetry of the small hole by being screwed in, and the threaded head also has a conical external thread which, when screwed in, engages with the internal thread of the large hole and induces relative displacement of the plate toward the bone.

Furthermore, a particular advantage is that the internal thread of the larger hole is disposed toward the fracture site of the bone and the crescent-shaped expansion is disposed away from the fracture, thereby making it possible to achieve fixation and compression using very few components in the smallest possible space.

The axes of the hole having the large diameter and the crescent-shaped expansion are disposed substantially perpendicularly to the top side of the bone plate and extend parallel to one another. This simplifies not only production of the bone plates, but also fixation to the particular part of the bone.

In a preferred embodiment, the ratio of the diameters between the hole having the large diameter D1 to the crescent-shaped expansion having the small diameter D2 is $0.5 < D2/D1 < 0.8$. This ensures that the centers of symmetry of the hole having the large diameter and the hole having the small diameter forming the crescent-shaped expansion are situated close to one another, thereby improving the stiffness and strength of the bone plate due to the reduced spatial requirement for the holes, and allowing the thickness of the bone plate to be reduced.

In a further preferred embodiment of the invention, the internal thread of the large hole is a fine-pitch thread, the pitch of which ranges between 0.5 mm and 1.2 mm. The conical external thread of the threaded head has a taper angle of 10° and 20°, and preferably 16°. This ensures that compression can be set precisely to the values required for the particular application.

In a further preferred embodiment, the device according to the invention also includes a drill guide for placing a hole in the bone in the center of symmetry of the hole having the small diameter, thereby making it possible to simply and easily maintain the desired orthogonal position with respect to the longitudinal axis of the bone plate.

Preferred materials for the bone plate and the bone screw are preferably biocompatible materials such as titanium, titanium alloys, steel, cobalt chromium alloys, plastic or composites. According to the invention, the bone plate and the bone screw can also be made of different materials having different mechanical properties.

Further advantages and details will become apparent from the description that follows, with reference to the attached drawings.

The invention is described in greater detail in the following, with reference to an exemplary embodiment.

BRIEF DESCRIPTION OF THE DRAWINGS

Shown are.

DETAILED DESCRIPTION OF THE INVENTION

Figure 1:
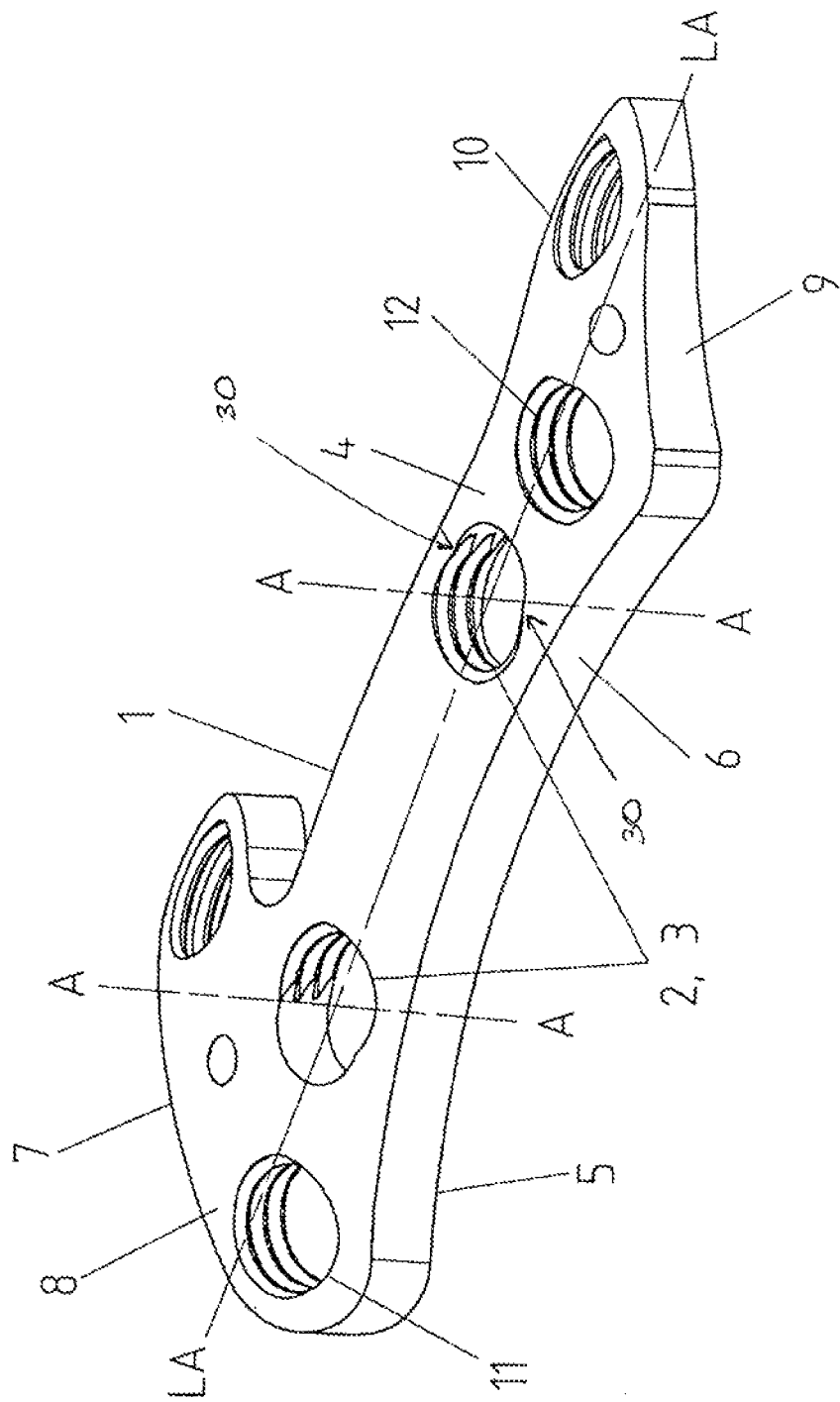
FIG. 1, a perspective view of the bone plate of the device according to the invention, depicting the positions of the holes in the bone plate, FIG. 2, an enlarged depiction of the fixation and compression hole formed of a hole having a larger diameter and a hole having a smaller diameter, in an enlarged view, FIG. 3, a sectional view of the bone plate with bone screws inserted in the bone, in the state before engagement of the external thread of the threaded head of the bone screw with the internal thread of the hole having the larger diameter, FIG. 4, a top view according to FIG. 3, FIG. 5, a sectional view of the bone plate with bone screws inserted in the bone, in the state after the external thread of the threaded head of the bone screw has been completely screwed into the internal thread of the hole having the large diameter, and FIG. 6, a top view according to FIG. 5.

FIG. 1 shows the bone plate 1 of the apparatus according to the invention for the fixed-angle fixation and compression of a fracture site of a bone using two opposing fixation and compression holes 2 and 3, which connect the top side 4 and the underside 5 of the bone plate 1. The bone plate 1 has a curvature that is matched to the shape and design of the bone parts to be treated. The fixation and compression holes 2 and 3 are located on a common longitudinal axis LA of the stem part 6 of the bone plate 1. Axes A thereof (AA and AB) are disposed substantially perpendicular to the longitudinal axis LA and extend parallel to one another.

The stem part 6 has a T-shaped expansion 8 at the end 7 thereof, and an L-shaped extension 10 at the other end 9 thereof. Both the expansion 8 and the extension 10 comprise two circular holes 11 having cylindrical internal threads 12 which serve to fix the bone plate 1 in the correct position on the bone parts to be treated. Other configurations of the bone plate are of course, also encompassed by the invention.

The apparatus according to the invention also includes bone screws 13 and a drill guide, which will be discussed in greater detail hereinafter.

The bone plate and bone screws are made of biocompatible materials such as titanium, titanium alloys, steel, cobalt-chromium alloys, plastic and composites.

Figure 2:
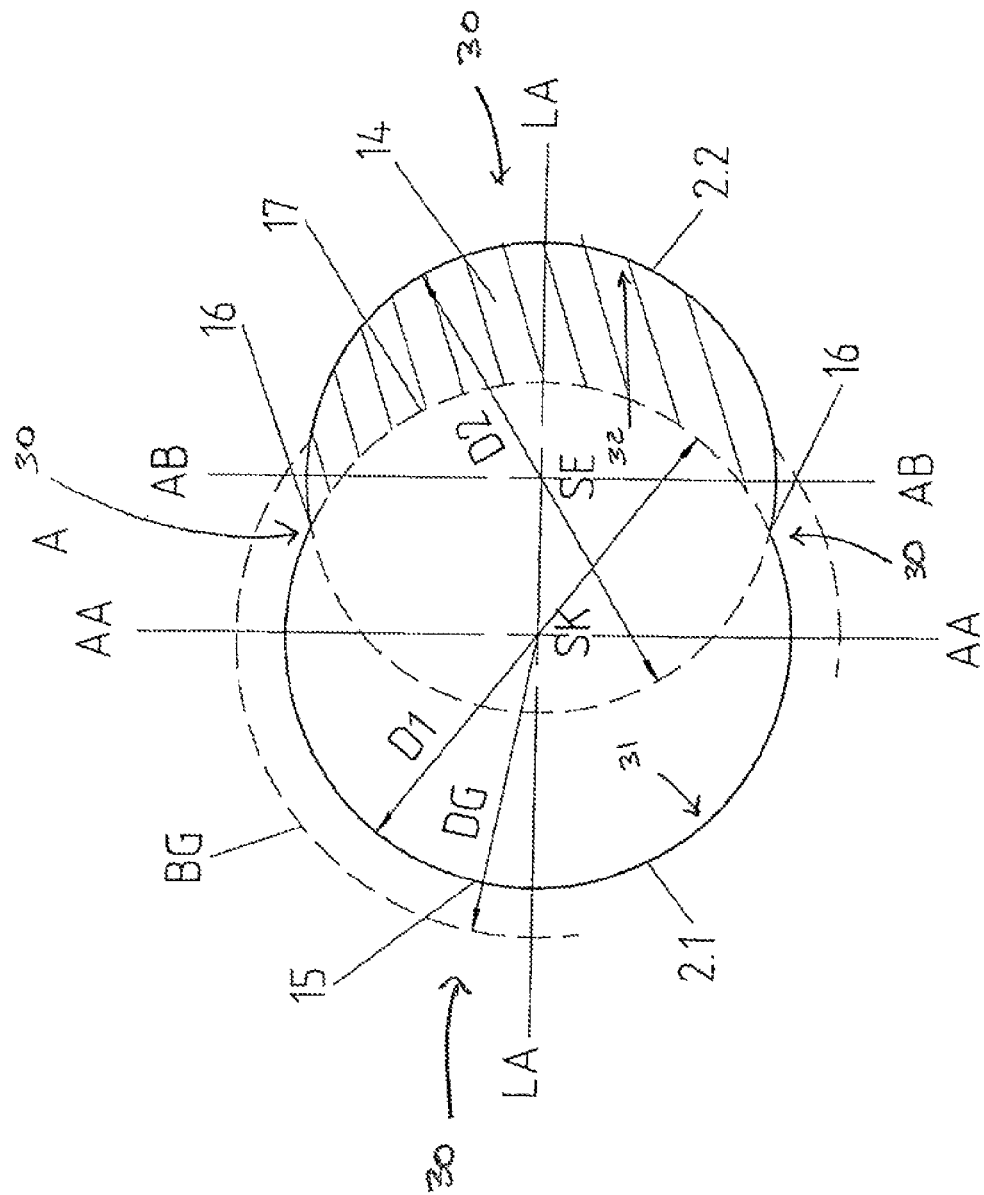

FIG. 2 shows an enlarged view of the fixation and compression hole, including a depiction of the geometric relationships and conditions.

The fixation and compression hole 2 is formed from a circular hole 2.1 having the diameter D1 and a circular hole 2.2 having the diameter D2, which are offset with respect to one another such that the circular hole 2.1 has a crescent-shaped expansion 14 in the direction away from the center of symmetry SK of the hole 2.1. The diameter D2 is smaller than the diameter D1. The two diameters D1 and D2 are related such that $0.5 < D2/D1 < 0.8$.

The center or axis of symmetry SK of the hole 2.1 and the center or axis of symmetry SE of the expansion 14 are located close to one another on the longitudinal axis LA of the bone plate 1 and are separated from each other by a distance A, which fulfills the following geometric condition $\frac{1}{18} D2 < A < \frac{1}{3} D2$. Respective vertical axes AA and AB pass through the respect centers of symmetry SK and SE.

The circular hole 2.1 is provided with a sector of a cylindrical internal thread, and more particularly with a fine-pitch thread 15, on the inner wall thereof. The fine-pitch thread 15 extends to the edges 16, at which the expansion 14 transitions into the circular hole 2.1, whereby the fine-pitch thread 15 describes a circular arc BG and forms an open part 17 that extends vertically laterally with respect to the expansion 14. Thus, as shown in FIGS. 1 and 2, each of the first and second fixation and compression holes 2, 3 has an inner most radially inwardly facing, perimeteral surface 30 that is defined by opposing first and second circular arcs 31, 32 that each subtend at an angle greater than 180 degrees. The first circular arc 31 has a first diameter and the second circular arc 32 has a smaller second diameter. The first and second circular arcs 31, 32 are joined together to form the edges 16, which face inwardly toward the longitudinal axis LA. The bone plate 1 has threads 15 along an entirety of the first circular arc 31. The bone plate 1 along the second circular arc 32 is without thread. As shown in FIG. 1, the first and second fixation and compression holes 2, 3 are oppositely oriented with respect to each other along the longitudinal axis LA so that the first circular arc 31 of the first fixation and compression hole 2 is located proximate to the first circular arc 31 of the second fixation and compression hole 3 and so that the second circular arc 32 of the first fixation and compression hole 2 is located distal from the second circular arc 32 of the second fixation and compression hole 3. As shown in FIG. 2, the first and second arcs 31, 32 of the fixation and compression holes 2, 3 define portions of the first circular hole 2.1 and the second circular hole 2.2, respectively.

Figure 3:
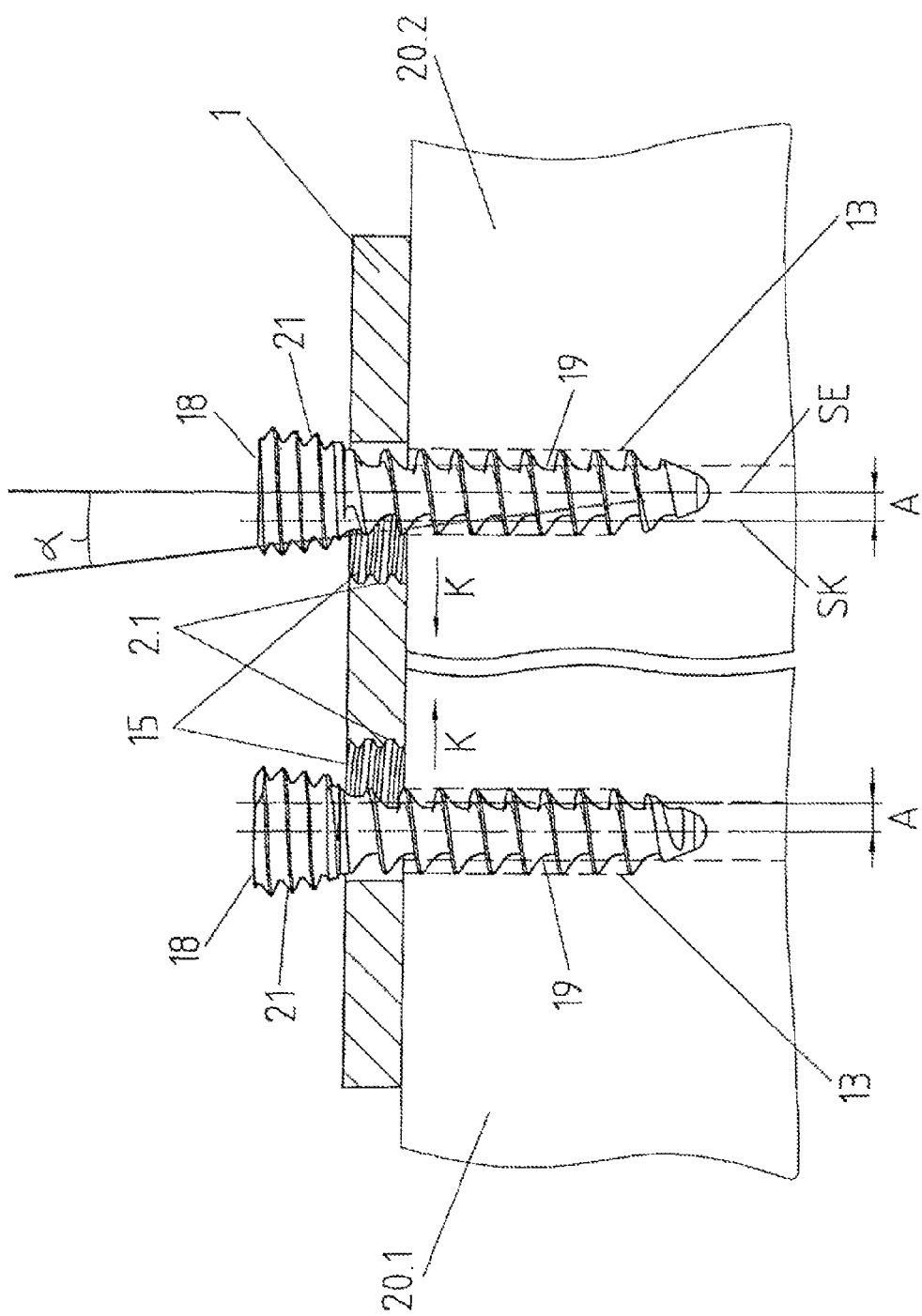

FIG. 3 shows a sectional view of the bone plate 1 in the state before the threaded head 18 of the bone screw 13 is screwed into the internal thread 15 in the circular hole 2.1. The threaded shank of the bone screw 13 has already been screwed partially into the pilot holes 19 in the bone parts 20.1 and 20.2 associated with the fracture. The pilot holes 19 are formed in the bone parts 20.1 and 20.2 using a drill guide, which is not depicted, in the center of symmetry SE of the hole 2.2. The center of symmetry SE lies on the axis LA, and the portion of the latter intersecting the crescent shaped expansion 14 is the axis of symmetry of the crescent-shaped expansion 14. The threaded head 18 comprises a conical external thread 21, which is matched to the internal thread 15 in the circular hole 2.1. The taper angle α of the external thread ranges between 10° and 20°, and more preferably is 16°. Reference is made to WO 2007/0255520A1 with respect to matching the conical external thread to the internal thread.

Since the centers of symmetry SK of the circular hole 2.1 and SE of the circular hole 2.2 are situated close to one another, further screwing-in allows the external thread 21 of the bone screw 13 to enter the open part 17 and engage with the internal thread 15, whereby the threaded head 18 is accommodated completely in the internal thread 15 in the screwed-in state. The bone screws 13 are retained securely in the pilot hole 19.

Figure 4:
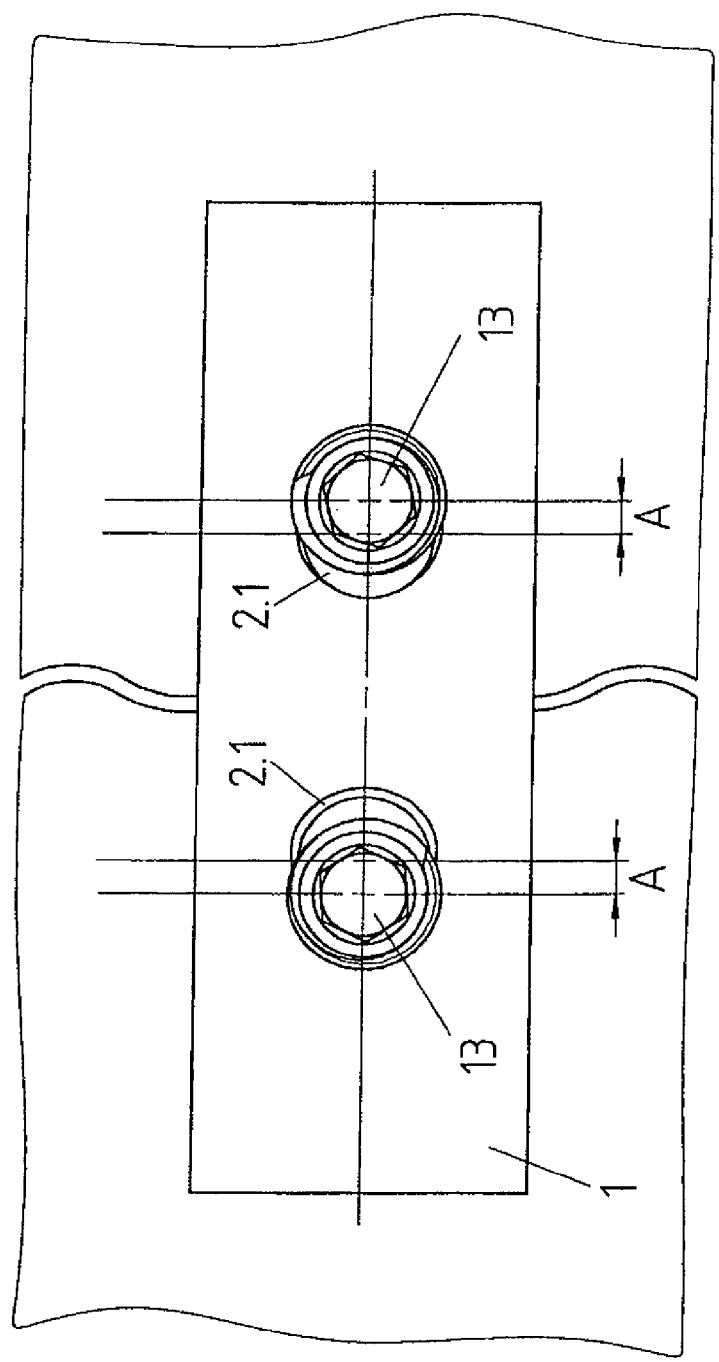

FIG. 4 shows this screwed-in state in the top view of the bone plate 1.

Figure 5:
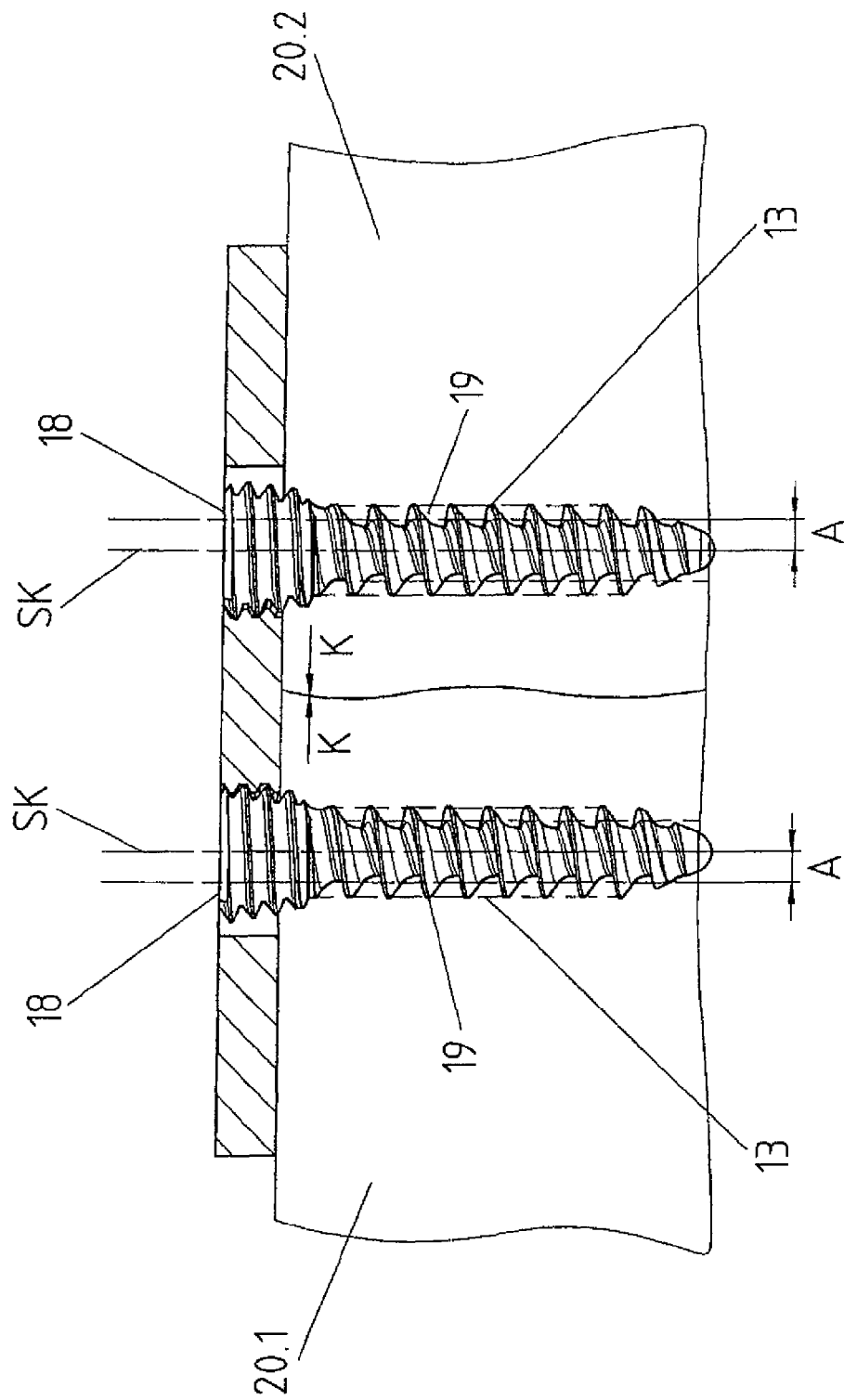

FIG. 5 shows the bone screws 13 in the fully screwed-in state. When screwed into the internal thread 15 of the hole 2.1, engagement of the conical threaded heads 18 of the two bone screws 13 with the internal threads 15 generates mutually opposed, forced movements K in the direction of the fracture site, which is therefore held under compression after the bones are pressed together. Relative motion between the bone and the plate has occurred in the longitudinal direction (i.e., parallel to the axis LA) so the axis of each bone screw is now coincident with the axis of symmetry SK instead of the axis of symmetry SE.

The bone screw 13 fixes and therefore exerts compression on the bone parts 20.1 and 20.2 by means of the conical external thread of the threaded head 18.

Figure 6:
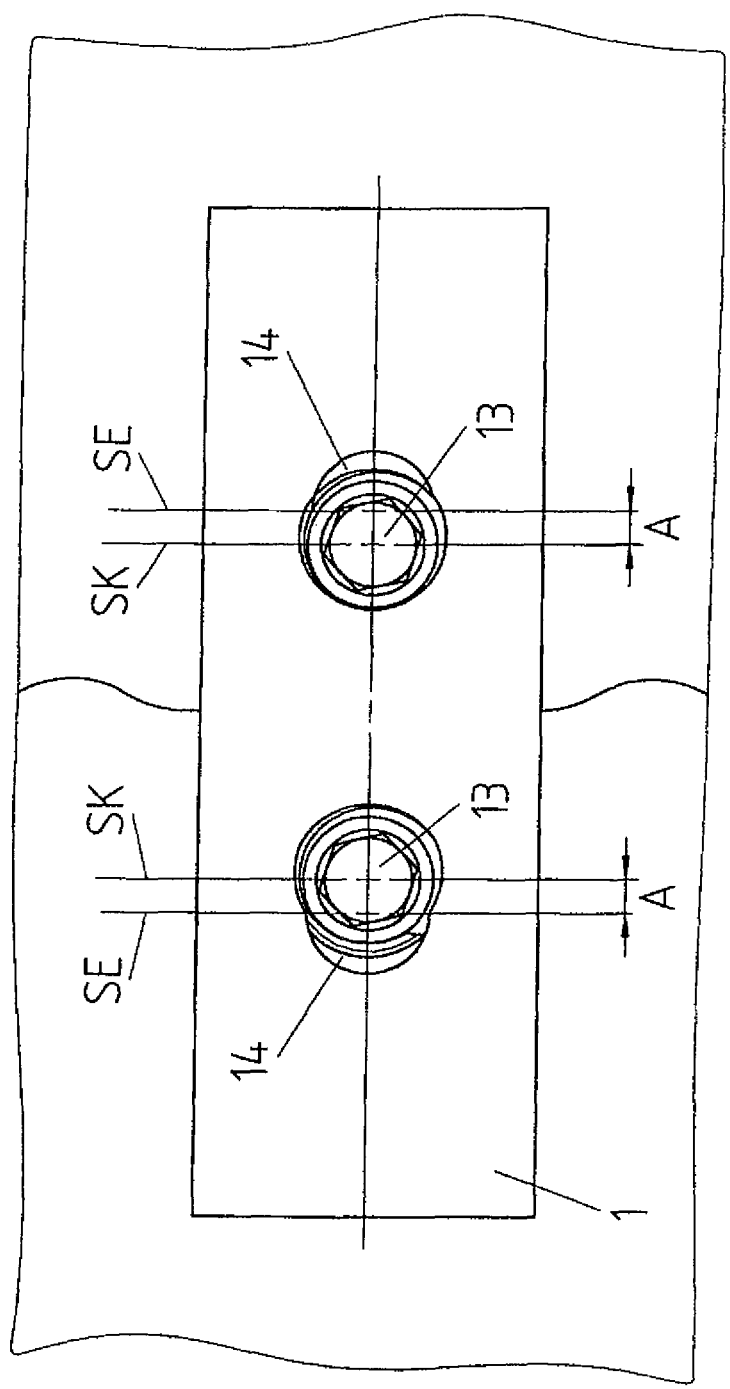

FIG. 6 shows the fully screwed-in bone screws 13.

The invention claimed is:

1. An apparatus for fixed-angle fixation and compression of a fracture site or osteotomy of a bone, the apparatus comprising:
   a bone plate that is elongated along a longitudinal axis and has a top side and an underside;
   the bone plate defining first and second fixation and compression holes that each extend through the bone plate from the top side to the underside, wherein the first and second fixation and compression holes are spaced apart from each other along the longitudinal axis;
   each of the first and second fixation and compression holes having an inner most radially inwardly facing, perimeteral surface comprising a first surface portion and a second surface portion, the first and second surface portions respectively being defined by opposing first and second circular arcs that each subtend an angle greater than 180 degrees, the first circular arc having a first diameter (D1) and the second circular arc having a smaller, second diameter (D2), wherein the first and second surface portions are joined together to form edges that face inwardly toward the longitudinal axis, each of the first and second surface portions forming a segment of a cylinder from the top side to the underside;
   wherein the bone plate comprises at least one thread along an entirety of the first surface portion;
   wherein the bone plate along the second surface portion is without a thread; and
   wherein the first and second fixation and compression holes are oppositely oriented with respect to each other along the longitudinal axis so that the first circular arc of the first fixation and compression hole is located proximate to the first circular arc of the second fixation and compression hole and so that the second circular arc of the first fixation and compression hole is located distal from the second circular arc of the second fixation and compression hole.

2. The apparatus according to claim 1, wherein the first and second surface portions of the first and second fixation and compression holes respectively define portions of a first circular hole extending through the bone plate having the first diameter and a second circular hole extending through the bone plate having the second diameter; and wherein the first and second circular holes intersect each other along the longitudinal axis.

3. An apparatus for fixed-angle fixation and compression of a fracture site or osteotomy of a bone, the apparatus comprising:
   a bone plate that is elongated along a longitudinal axis and has a top side and an underside;
   the bone plate defining first and second fixation and compression holes that each extend through the bone plate from the top side to the underside, wherein the first and second fixation and compression holes are spaced apart from each other along the longitudinal axis;
   each of the first and second fixation and compression holes having an inner most radially inwardly facing, perimeteral surface comprising a first surface portion and a second surface portion, the first and second surface portions respectively being defined by opposing first and second circular arcs that each subtend an angle greater than 180 degrees, the first circular arc having a first diameter (D1) and the second circular arc having a smaller, second diameter (D2), wherein the first and second surface portions are joined together to form edges that face inwardly toward the longitudinal axis;
   wherein the bone plate comprises at least one thread along an entirety of the first surface portion;
   wherein the bone plate along the second surface portion is without a thread; and
   wherein the first and second fixation and compression holes are oppositely oriented with respect to each other along the longitudinal axis so that the first circular arc of the first fixation and compression hole is located proximate to the first circular arc of the second fixation and compression hole and so that the second circular arc of the first fixation and compression hole is located distal from the second circular arc of the second fixation and compression hole;
   wherein the first and second surface portions of the first and second fixation and compression holes respectively define portions of a first circular hole extending through the bone plate having the first diameter and a second circular hole extending through the bone plate having the second diameter; and wherein the first and second circular holes intersect each other along the longitudinal axis;
   wherein the first circular hole has an axis of symmetry that intersects with the longitudinal axis and wherein the second circular hole has an axis of symmetry that intersects with the longitudinal axis; wherein a first vertical axis coextends with the axis of symmetry of the first circular hole and wherein a second vertical axis coextends with the axis of symmetry of the second circular hole; wherein the first vertical axis and the second vertical axis are parallel to each other; and wherein the axis of symmetry of the first circular hole and the axis of symmetry of the second circular hole are separated from each other along the longitudinal axis by a distance (A) and wherein $1/18(D2) < A < 1/3(D2)$.

4. The apparatus according to claim 3, wherein D1 and D2 are sized such that $0.5 < D2/D1 < 0.8$.

5. The apparatus according to claim 4, further comprising first and second bone screws, each having a threaded shank and a conical threaded head.

6. The apparatus according to claim 5, wherein the conical threaded head of each of the first and second bone screws mates with the at least one thread disposed on said first surface portion of a respective one of said first and second fixation and compression holes.

7. The apparatus according to claim 6, whereby the apparatus is configured such that inserting the first and second bone screws into the first and second fixation and compression holes, respectively, along the second vertical axis of the respective one of the first and second fixation and compression holes, and turning the first and second bone screws, causes the conical threaded head of each of the first and second bone screws to engage with the at least one thread of the first surface portion of the respective one of the first and second fixation and compression holes, which causes the first and second bone screws to move towards each other along the longitudinal axis until each of the first and second bone screws is oriented along the first vertical axis of the respective one of the first and second fixation and compression holes, thereby generating mutually opposed, forced movements in a direction of the fracture site or osteotomy, which thereby is held under compression.

8. The apparatus according to claim 7, wherein the bone plate comprises a stem part having a T-shaped expansion at one end and an L-shaped extension at an opposite end.

9. An apparatus for fixed-angle fixation and compression of a fracture site or osteotomy of a bone, the apparatus comprising:
- a bone plate that is elongated along a longitudinal axis and has a top side and an underside;
- the bone plate defining first and second fixation and compression holes that each extend through the bone plate from the top side to the underside, wherein the first and second fixation and compression holes are spaced apart from each other along the longitudinal axis;
- each of the first and second fixation and compression holes having an inner most radially inwardly facing, perimeteral surface comprising a first surface portion and a second surface portion, the first and second surface portions respectively being defined by opposing first and second circular arcs that each subtend an angle greater than 180 degrees, the first circular arc having a first diameter (D1) and the second circular arc having a smaller, second diameter (D2), wherein the first and second surface portions are joined together to form edges that face inwardly toward the longitudinal axis;
- wherein the bone plate comprises at least one thread along an entirety of the first surface portion;
- wherein the bone plate along the second surface portion is without a thread;
- wherein the first and second fixation and compression holes are oppositely oriented with respect to each other along the longitudinal axis so that the first circular arc of the first fixation and compression hole is located proximate to the first circular arc of the second fixation and compression hole and so that the second circular arc of the first fixation and compression hole is located distal from the second circular arc of the second fixation and compression hole;
- wherein the first and second surface portions of the first and second fixation and compression holes respectively define portions of a first circular hole extending through the bone plate having the first diameter and a second circular hole extending through the bone plate having the second diameter; and wherein the first and second circular holes intersect each other along the longitudinal axis;
- wherein the first circular hole has an axis of symmetry that intersects with the longitudinal axis and wherein the second circular hole has an axis of symmetry that intersects with the longitudinal axis; wherein a first vertical axis coextends with the axis of symmetry of the first circular hole and wherein a second vertical axis coextends with the axis of symmetry of the second circular hole; wherein the first vertical axis and the second vertical axis are parallel to each other; and wherein the axis of symmetry of the first circular hole and the axis of symmetry of the second circular hole are separated from each other along the longitudinal axis by a distance (A) and wherein $1/18(D2) < A < 1/3(D2)$;
- wherein D1 and D2 are sized such that $0.5 < D2/D1 < 0.8$;
- further comprising first and second bone screws, each having a threaded shank and a conical threaded head;
- wherein the conical threaded head of each of the first and second bone screws mates with the at least one thread disposed on said first surface portion of a respective one of said first and second fixation and compression holes;
- whereby the apparatus is configured such that inserting the first and second bone screws into the first and second fixation and compression holes, respectively, along the second vertical axis of the respective one of the first and second fixation and compression holes, and turning the first and second bone screws, causes the conical threaded head of each of the first and second bone screws to engage with the at least one thread of the first surface portion of the respective one of the first and second fixation and compression holes, which causes the first and second bone screws to move towards each other along the longitudinal axis until each of the first and second bone screws is oriented along the first vertical axis of the respective one of the first and second fixation and compression holes, thereby generating mutually opposed, forced movements in a direction of the fracture site or osteotomy, which thereby is held under compression; and
- wherein the bone plate comprises a stem part having a T-shaped expansion at one end and an L-shaped extension at an opposite end; and
- further comprising two threaded circular holes vertically extending from the top side to the underside in the T-shaped expansion and two threaded circular holes vertically extending from the top side to the underside in the L-shaped extension.

* * * * *

UNITED STATES PATENT AND TRADEMARK OFFICE
CERTIFICATE OF CORRECTION

| | | |
|---|---|---|
| PATENT NO. | : 8,940,026 B2 | Page 1 of 1 |
| APPLICATION NO. | : 13/263037 | |
| DATED | : January 27, 2015 | |
| INVENTOR(S) | : Martin Hilse et al. | |

It is certified that error appears in the above-identified patent and that said Letters Patent is hereby corrected as shown below:

In the Claims:

In claim 2, at column 5, line 58: "hone" should instead read --bone--.

In claim 5, at column 6, line 54: "hone" should instead read --bone--.

Signed and Sealed this
Twelfth Day of May, 2015

Michelle K. Lee
*Director of the United States Patent and Trademark Office*